United States Patent [19]

Bovenberg et al.

[11] Patent Number: 5,747,285
[45] Date of Patent: May 5, 1998

[54] **DNA COMPRISING REGULATORY REGIONS FROM GENE Y OF *PENICILLIUM CHRYSOGENUM***

[75] Inventors: Roelof Ary Lans Bovenberg, Rotterdam; Adrianus Wilhelmus Hermanus Vollebregt; Pieter Van Solingen, both of Naaldwijk, all of Netherlands

[73] Assignee: Gist-Brocades, NV., Netherlands

[21] Appl. No.: 207,900

[22] Filed: Mar. 8, 1994

Related U.S. Application Data

[63] Continuation of Ser. No. 855,418, Mar. 20, 1992, abandoned, which is a continuation-in-part of Ser. No. 305,532, Feb. 1, 1989, Pat. No. 5,108,918.

[30] Foreign Application Priority Data

Dec. 23, 1991 [EP] European Pat. Off. ............. 91203400

[51] Int. Cl.$^6$ ......................... C12N 15/62; C12N 15/80
[52] U.S. Cl. ...................... 435/69.7; 435/69.1; 536/23.4; 536/23.5
[58] Field of Search ........................ 435/69.1, 252.3, 435/320.1; 536/23.7, 23.5, 24.1, 23.4

[56] References Cited

FOREIGN PATENT DOCUMENTS 0233715  8/1987  European Pat. Off. .
0336446A1  7/1989  European Pat. Off. .

OTHER PUBLICATIONS

B. Lewin, "GENES", published 1987 by John Wiley & Sons. pp. 193–195.
*Chemical Abstracts* (1985) 105:222438z, p. 421.
*Chemical Abstracts* (1988) 108:51779s, p. 324.
"Two genes involved in penicillin biosynthesis are linked in a 5.1 Kb Sal I fragment in the genome of *Penicillium chrysogenum*", Diez et al., *Mol. Gen. Genet* 218:572–576, (1989).
*Genetics and Microbiology of Industrial Microorganisms,* Veenstra et al., Hershberger and Queener ed., ASM publications, pp. 262–269.

*Primary Examiner*—John Ulm
*Attorney, Agent, or Firm*—McDonnell Boehnen Hulbert & Berghoff

[57] ABSTRACT

A gene expression system and a protein secretion system for eukaryotic, especially fungal, microorganisms has been provided for.

17 Claims, 3 Drawing Sheets

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 1514 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( B ) STRAIN: Penicillium chrysogenum ( i x ) FEATURE:
        ( A ) NAME/KEY: exon
        ( B ) LOCATION: 427..552

( i x ) FEATURE:
        ( A ) NAME/KEY: intron
        ( B ) LOCATION: 553..628

( i x ) FEATURE:
        ( A ) NAME/KEY: exon
        ( B ) LOCATION: 629..718

( i x ) FEATURE:
        ( A ) NAME/KEY: intron
        ( B ) LOCATION: 719..786

( i x ) FEATURE:
        ( A ) NAME/KEY: exon
        ( B ) LOCATION: 787..846

( i x ) FEATURE:
        ( A ) NAME/KEY: CDS
        ( B ) LOCATION: join(427..552, 629..718, 787..846)

(D) OTHER INFORMATION: /codon_start= 427
/ product= "Antifungal protein (preprotein)"

(ix) FEATURE:
(A) NAME/KEY: sig_peptide
(B) LOCATION: 427..537

(ix) FEATURE:
(A) NAME/KEY: mat_peptide
(B) LOCATION: 538..846
(C) IDENTIFICATION METHOD: experimental
(D) OTHER INFORMATION: /product= "Antifungal protein"
/ evidence= EXPERIMENTAL (xi) SEQUENCE DESCRIPTION: SEQ ID NO:1:

```
GCCAGTCACC GTGTCAAGCG TTCAGCCGTT TCTCTGCTTT TTAGGAAATT GATTACCACT      60

AGGTAAGCCC AAAAATATCT TCCTGGTAAA CAAGTAGTGC ATTCTTACCC CGGAGGCTGA     120

AGCAGGTAAG GGATTTTGGA GAGACCCCAC CCGTAAGAAT ATACCAGCCA AGAGGTCCAG     180

TATCCTGAAG TATGTGAGGC ATTAATGTCA TTGGAGAAGT CATGCAATCC ATAAGCTGCC     240

ACCCCCAAGA TGACTGCATT GGACCTGAGC ATTGTATGTG TCACCTTTCA CACAGAGCTC     300

ATGATCTGGT TTATAAAGGC GGCTTCATGA CCCTCAATTC CATATAGTAT CACTCCCATC     360

ACAGCATTTC GATATCTTCA ACCACTTTAA CCTTCTCCAG AGGATCATCA TCTCAAGCCC     420

TTCATA ATG CAA ATC ACC ACA GTT GCC CTT TTT CTC TTC GCT GCA ATG       468
       Met Gln Ile Thr Thr Val Ala Leu Phe Leu Phe Ala Ala Met
       -37     -35                 -30                     -25

GGC GGG GTA GCC ACC CCC ATT GAG TCT GTA TCA AAC GAC CTC GAT GCC      516
Gly Gly Val Ala Thr Pro Ile Glu Ser Val Ser Asn Asp Leu Asp Ala
        -20                 -15                     -10

AGG GCT GAG GCC GGT GTC CTG GCC AAA TAC ACC GGA GTGAGTAAAC            562
Arg Ala Glu Ala Gly Val Leu Ala Lys Tyr Thr Gly
     -5              1                   5

ATCAATATCC CATACCTTAA GTACTCACTT GGGAATCGCG ACTAACGGTT CGGGACCACA     622

ACTCAG AAA TGC ACC AAA TCT AAG AAC GAA TGT AAA TAC AAG AAC GAT       670
       Lys Cys Thr Lys Ser Lys Asn Glu Cys Lys Tyr Lys Asn Asp
                    10                      15

GCT GGA AAG GAC ACT TTT ATC AAG TGC CCC AAG TTT GAT AAC AAG AAG      718
Ala Gly Lys Asp Thr Phe Ile Lys Cys Pro Lys Phe Asp Asn Lys Lys
 20                  25                  30                  35

GTAGAATATC AATCATTCGG AAGTAGCCAT CTGAATCGAT TTCGTGCTAA TCTCGCTCTT     778

TTTTCCAG TGC ACC AAG GAT AAT AAC AAA TGT ACC GTC GAC ACC TAC AAC     828
         Cys Thr Lys Asp Asn Asn Lys Cys Thr Val Asp Thr Tyr Asn
                         40                      45

AAC GCT GTC GAT TGT GAC TAGATGGTCT CTGCGATCAC CAGGGCATTT              876
Asn Ala Val Asp Cys Asp
 50              55

AATGGTTTTT GGTTCCCTTC TTGTTGGTGA TATGCGAGAT GCCCTGTGAT TCTCGAAGCT     936

TACTACCCTA CACCCACAAG GAACTCGGAA CCAAGGAACT GCTCGGTGGG TGATACATAT     996

ACACCCAGTA TCTATCCAGC TTCAATTTTC GGCGAATTTT GTTTCTTATT TCATAAAGAC    1056

ACTCGTTTGA TATCTAGCTA GATATTGTTG CTCATCAACG AAATGGTTGT AGATTATCGA    1116

ATATATCCAG CATCTTTTGA TCGTAGTCGG AAGTGAAATG GAGTACTATG ATACGACACA    1176

TGTACATTGT AAGCAGAAAT AGGCTAGAGG GATAACTATC AAACTGCTGC AGCAGCGCTA    1236

CTCTTGCTTC TGTGCGGGGT CAAACTTGTT TGCGAGCCGG ACTGCCAAAT CAGGGTCTGG    1296

GTAATGCTGG GGGCCGATTC CCTGTTATGC GGTAAGGATT AACTGGGGTT CTCAAAATGT    1356

TTCACACAGC CACTTCGTTA TTCCTTATAC CTGCCAAAAT CCCGCAATTT AATTCCTTAG    1416
```

```
TACACCCGTT ATACATCTAT CGCTGATAAG GTTTATCATA GGTACAATAG CTTTGATTAT    1476

AGGGACACGT CCAATGCTTA AATGCAATTT CCTTAACA                           1514
```

( 2 ) INFORMATION FOR SEQ ID NO:2:

( i ) SEQUENCE CHARACTERISTICS:
        ( A ) LENGTH: 92 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gln Ile Thr Thr Val Ala Leu Phe Leu Phe Ala Ala Met Gly Gly
-37     -35                     -30                 -25

Val Ala Thr Pro Ile Glu Ser Val Ser Asn Asp Leu Asp Ala Arg Ala
    -20             -15                     -10

Glu Ala Gly Val Leu Ala Lys Tyr Thr Gly Lys Cys Thr Lys Ser Lys
-5                   1               5                       10

Asn Glu Cys Lys Tyr Lys Asn Asp Ala Gly Lys Asp Thr Phe Ile Lys
            15                  20                      25

Cys Pro Lys Phe Asp Asn Lys Lys Cys Thr Lys Asp Asn Asn Lys Cys
            30                  35                  40

Thr Val Asp Thr Tyr Asn Asn Ala Val Asp Cys Asp
    45                  50              55
```

( 2 ) INFORMATION FOR SEQ ID NO:3:

( i ) SEQUENCE CHARACTERISTICS:
        ( A ) LENGTH: 355 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( v i ) ORIGINAL SOURCE:
        ( A ) ORGANISM: Penicillium chrysogenum ( x i ) SEQUENCE DESCRIPTION: SEQ ID NO:3:

```
ATGCAAATCA CCACAGTTGC CCTTTTTCTC TTCGCTGCAA TGGGCGGGGT AGCCACCCCC    60

ATTGAGTCTG TATCAAACGA CCTCGATGCC AGGGCTGAGG CCGGTGTCCT GGCCAAATAC   120

ACCGGAAAAT GCACCAAATC TAAGAACGAA TGTAAATACA AGAACGATGC TGGAAAGGAC   180

ACTTTTATCA AGTGCCCCAA GTTTGATAAC AAGAAGTGCA CCAAGGATAA TAACAAATGT   240

ACCGTCGACA CCTACAACAA CGCTGTCGAT TGTGACTAGA TGGTCTCTGC GATCACCAGG   300

GCATTTAATG GTTTTGGTT CCCTTCTTGT TGGTGATATG CGAGATGCCC TGTGA          355
```

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Penicillium chrysogenum ( x i ) SEQUENCE DESCRIPTION: SEQ ID NO:4:

Ala Lys Tyr Thr Gly Lys Xaa Thr Lys Ser Lys Asn Glu Xaa Lys Tyr
1               5                       10                      15

Lys Asn Asp Ala Gly
              20

( 2 ) INFORMATION FOR SEQ ID NO:5:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        ( C ) INDIVIDUAL ISOLATE: AB2277

( x i ) SEQUENCE DESCRIPTION: SEQ ID NO:5:

CCCGGGACTA GTATGCAAAT CACCACAGTT GCC                          33

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        ( C ) INDIVIDUAL ISOLATE: AB2278

( x i ) SEQUENCE DESCRIPTION: SEQ ID NO:6:

CCCGGGACTA GTATGACCCT CAATTCCATA TAG                          33

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        ( C ) INDIVIDUAL ISOLATE: AB2280

( x i ) SEQUENCE DESCRIPTION: SEQ ID NO:7:

CCCGGGGAT CCTCACAGGG CATCTCGCAT ATC                           33

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
    ( C ) INDIVIDUAL ISOLATE: AB2308

( x i ) SEQUENCE DESCRIPTION: SEQ ID NO:8:

CCCGGGACTA GTGCCAGTCA CCGTGTCAAG CGT　　　　　　　　　　　33

( 2 ) INFORMATION FOR SEQ ID NO:9:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (synthetic)

( i i i ) HYPOTHETICAL: NO ( v i ) ORIGINAL SOURCE:
    ( C ) INDIVIDUAL ISOLATE: AB2309

( x i ) SEQUENCE DESCRIPTION: SEQ ID NO:9:

CCCGGGACTA GTCCACCCGT AAGAATATAC CAG　　　　　　　　　　　33

( 2 ) INFORMATION FOR SEQ ID NO:10:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (synthetic)

( i i i ) HYPOTHETICAL: NO ( v i ) ORIGINAL SOURCE:
    ( C ) INDIVIDUAL ISOLATE: AB2312

( x i ) SEQUENCE DESCRIPTION: SEQ ID NO:10:

CCCGGGACTA GTTTGGACCT GAGCATTGTA TGT　　　　　　　　　　　33

( 2 ) INFORMATION FOR SEQ ID NO:11:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (synthetic)

( i i i ) HYPOTHETICAL: NO ( v i ) ORIGINAL SOURCE:
    ( C ) INDIVIDUAL ISOLATE: AB2313

( x i ) SEQUENCE DESCRIPTION: SEQ ID NO:11:

CCCGGGGGAT CCGATGGGAG TGATACTATA TGG　　　　　　　　　　　33

( 2 ) INFORMATION FOR SEQ ID NO:12:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (synthetic)

( i i i ) HYPOTHETICAL: NO ( v i i ) IMMEDIATE SOURCE:
    ( B ) CLONE: AB2314

( x i ) SEQUENCE DESCRIPTION: SEQ ID NO:12:

CCCGGGACTA GTATATCCCA TACCTTAAGT ACT    33

( 2 ) INFORMATION FOR SEQ ID NO:13:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        ( C ) INDIVIDUAL ISOLATE: AB2315

( x i ) SEQUENCE DESCRIPTION: SEQ ID NO:13:

CCCGGGGGAT CCAGTACTTA AGGTATGGGA TAT    33

( 2 ) INFORMATION FOR SEQ ID NO:14:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        ( C ) INDIVIDUAL ISOLATE: AB2316

( x i ) SEQUENCE DESCRIPTION: SEQ ID NO:14:

CCCGGGGGAT CCTATTTACA TTCGTTCTTA GAT    33

( 2 ) INFORMATION FOR SEQ ID NO:15:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        ( C ) INDIVIDUAL ISOLATE: AB2317

( x i ) SEQUENCE DESCRIPTION: SEQ ID NO:15:

CCCGGGGGAT CCGTTCCTTG TGGGTGTAGG GTA    33

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
    ( C ) INDIVIDUAL ISOLATE: AB2319

( x i ) SEQUENCE DESCRIPTION: SEQ ID NO:16:

CCCGGGGGAT CCACGATCAA AAGATGCTGG ATA    33

( 2 ) INFORMATION FOR SEQ ID NO:17:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        ( C ) INDIVIDUAL ISOLATE: AB2425

( x i ) SEQUENCE DESCRIPTION: SEQ ID NO:17:

CCCGGGACTA GTTATAGTAT CACTCCCATC ACA    33

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        ( C ) INDIVIDUAL ISOLATE: AB2426

( x i ) SEQUENCE DESCRIPTION: SEQ ID NO:18:

GGGCTTGAGA TGATGATC    18

( 2 ) INFORMATION FOR SEQ ID NO:19:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( v i ) ORIGINAL SOURCE:
        ( C ) INDIVIDUAL ISOLATE: reverse sequencing primer ( x i ) SEQUENCE DESCRIPTION: SEQ ID NO:19:

AACAGCTATG ACCATG    16

( 2 ) INFORMATION FOR SEQ ID NO:20:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:20:

Thr Thr Ala Tyr Cys Gln Leu Pro Asn Gly Ala Leu Gln Gly Gln Asn
1               5                   10                  15

Trp Asp ( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( x i ) SEQUENCE DESCRIPTION: SEQ ID NO:21:

CARGGNCARA AYTGGGAY                                                      18

( 2 ) INFORMATION FOR SEQ ID NO:22:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:22:

Met Leu His Ile Leu Xaa Gln Gly Thr Pro Phe Glu Ile Gly Tyr Glu
1               5                   10                  15

His Gly Ser Ala Ala Lys Ala Val Ile Ala
                20                  25

( 2 ) INFORMATION FOR SEQ ID NO:23:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:23:

Thr Thr Ala Tyr Cys Gln Leu Pro Asp Gly Ala Leu Gln Gly Gln Asn
1               5                   10                  15

Trp Asp Phe Phe Ser Ala Thr Lys Gln Ala
                20                  25

( 2 ) INFORMATION FOR SEQ ID NO:24:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (synthetic)

```
( i i i ) HYPOTHETICAL: NO ( x i ) SEQUENCE DESCRIPTION: SEQ ID NO:24:

GGAACGGCAC  TGGTCAACTT  GGCCATGGTG  GGTAGTTAAT  GGTATG                    4 6
```

DNA COMPRISING REGULATORY REGIONS FROM GENE Y OF *PENICILLIUM CHRYSOGENUM*

This application is a continuation of application Ser. No. 07/855,418, filed Mar. 20, 1992, now abandoned, which is a continuation in part of application Ser. No. 07/305,532, filed Feb. 1, 1989, now U.S. Pat. No. 5,108,918, which disclosure is hereby incorporated by reference.

INTRODUCTION

1. Field of the Invention

This application relates to a gene expression and protein secretion system for eukaryotic cells, particularly fungal cells.

2. Background

Commercial production of proteins is a main objective of industrial biotechnology. To that end a range of organisms are used, most of them being microorganisms, especially bacteria of the species Escherichia, Bacillus, Actinomycetes; yeasts of the species Saccharomyces and Kluyveromyces; and filamentous fungi of the species Aspergillus and Trichoderma. The ability to introduce and express novel DNA sequences into living cells has created many new possibilities for protein production by microorganisms.

The development of reliable gene transfer systems for filamentous fungi has greatly stimulated interests for application of these microorganisms in commercial protein production processes. These interests are explained by the following facts:

1) by nature, filamentous fungi are able to synthesize and secrete large amounts of proteins;
2) several fungi have a long record of industrial use and are generally recognized as safe (GRAS) production organisms;
3) considerable knowledge and experience is available on large scale fermentation and processing of fungal cultures;
4) the structure of heterologous proteins produced in filamentous fungi closely mimics (or is identical to) the authentic structure of these proteins with regard to termini, modification and folding. This is often not achieved by using bacterial or yeast cells as hosts for heterologous gene expression;
5) the stability of transformed rDNA in fungal strains.

Despite all of these favorable characteristics, only a limited number of filamentous fungus species are in use in protein production processes. Furthermore, expression of heterologous proteins in these filamentous fungus species is generally not as efficient as expression of homologous proteins. Thus, systems which allow for efficient gene expression and protein secretion and which extend the repertoire of filamentous fungus hosts for protein production are in great demand, particularly for application to *Penicillium chrysogenum*. *P. chrysogenum* is the fungus used world-wide for over 40 years for commercial production of penicillin. As a consequence, great experience has been obtained in fermentation of *P. chrysogenum*. Moreover, non-penicillin producing mutants of *P. chrysogenum* are available which avoid the problem of penicillin contamination of the produced protein. Up to now, obtention of such an efficient gene expression and protein secretion system has eluded the art.

RELEVANT LITERATURE

Filamentous fungus species such as *Aspergillus niger, Aspergillus oryzae, Mucor miehei* and *Trichoderma reesei* are used in the industrial production of enzymes, e.g. for use in the food industry. See, for example, Strijkert (Antonie van Leeuwenhoek 53 (1987), 357–362) and Unkles (in: Molecular and Genetic Aspects of Nitrate Assimilation, Wray, J. L. and Kinghorn, J. R. (eds), 1989, 341–363, Oxford Science Publications, Oxford, UK). *Aspergillus niger* (D. Cullen et al., Biotechnology 5 (1987), 369–376; A. Haarki et al., Biotechnology 7 (1989), 596600; and EP-A-420358), *Aspergillus nidulans* (G. L. Gray et al., Gene 48 (1986), 41–53; and D. I. Gwynne et al., Biotechnology (1987), 713–719), and *Aspergillus oryzae* (T. Christensen et al., Biotechnology 6 (1988), 1419–1422) have also been used for expression of various heterologous proteins for use in food and detergents and in pharmaceutical industry.

The expression systems used employ sequences for initiation and termination of transcription and sequences for processing and secretion of the expressed protein obtained from *A. niger* glucoamylase (gla) gene, the *T. reesei* cellobiohydrolase (cbhI) gene, the *A. oryzae* α-amylase gene and the *A. nidulans* alcA gene (D. I. Gwynne et al., supra; A. Haarki et al., supra; and T. Christensen et al., supra).

SUMMARY OF THE INVENTION

An efficient protein expression system is provided employing filamentous fungus species as hosts, particularly *Penicillium chrysogenum*. The expression system provides for DNA sequences for efficient initiation of transcription (promoter) and translation, DNA sequences for efficient termination of transcription and 3' mRNA processing (terminator), and DNA sequences necessary for efficient processing and secretion of the expressed protein.

BRIEF DESCRIPTION OF THE SEQUENCE LISTINGS

Figure 1:
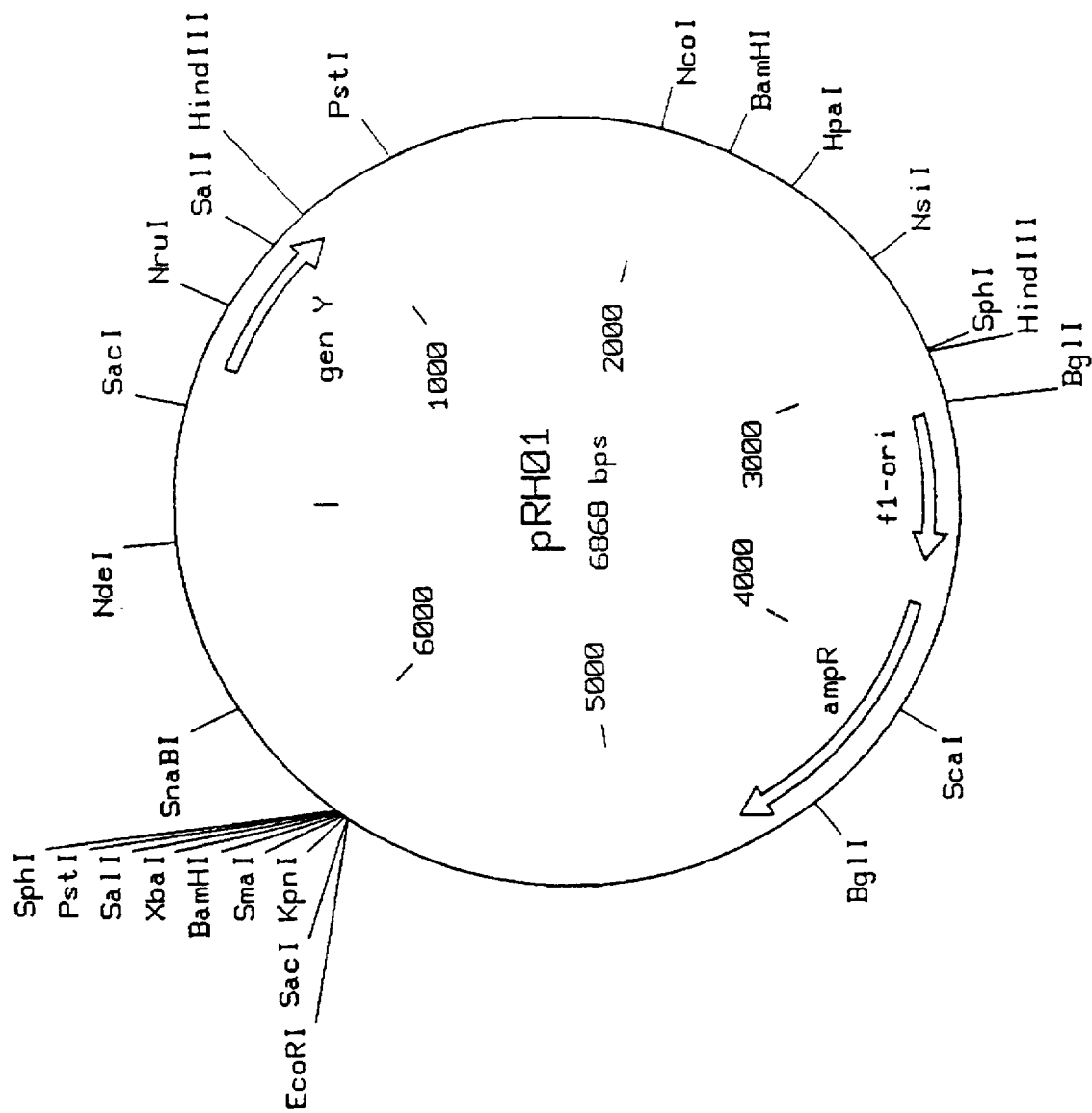
FIG. 1 shows a schematic representation of plasmid pRHO1.

Sequence Listing 1 (SEQ ID NO: 1) is the nucleotide sequence of the Y gene of *P. chrysogenum* and derived sequence of amino acids.

Sequence Listing 2 (SEQ ID NO: 2) is the amino acid sequence of Y of *P. chrysogenum*.

Sequence Listing 3 (SEQ ID NO: 3) is a partial nucleotide sequence of Y cDNA.

Sequence Listing 4 (SEQ ID NO: 4) is a partial N-terminal amino acid sequence of Y of *P. chrysogenum*.

Sequence Listings 5–19 (SEQ ID NO: 5 through SEQ ID NO: 19) are nucleotide sequences of gene Y derived synthetic oligonucleotides.

SEQ ID NO: 20 is the amino acid sequence of the 29 kD protein.

SEQ ID NO: 21 is a synthetic oligonucleotide encoding part of the amino terminal of the 29 kD protein.

SEQ ID NO: 22 is the amino acid sequence of the 10 kD protein.

SEQ ID NO: 23 is the extended sequence of the 29 kD protein.

SEQ ID NO: 24 is a synthetic oligonucleotide.

DESCRIPTION OF THE SPECIFIC EMBODIMENTS

The present invention provides an efficient gene expression and protein secretion system for eukaryotic microorganisms, especially for filamentous fungi: transcription initiation and termination sequences comprising nucleotide sequences depicted in Sequence Listing 1 (SEQ ID NO: 1) from nucleotide 1 up to nucleotide 426 and from nucleotide 850 up to nucleotide 1514, respectively, or essentially the same nucleotide sequences, or functional parts thereof. Typically, these regulating sequences originate from gene Y. Also the use of the regulating sequences in a transformed host, particularly in a filamentous fungus host, preferably in P. chrysogenum, for the expression of a gene, by the fusion of the open reading frame of said gene to said regulating sequences has been provided for. Finally, secretion signal encoding sequences comprising the nucleotide sequences depicted in Sequence Listing 1 (SEQ ID NO: 1) from nucleotide 427 up to 537 or essentially the same nucleotide sequences, or functional parts thereof, and the use of these secretion signal encoding sequences, in a transformed host, particularly in a filamentous fungus host, preferably in P. chrysogenum, for the secretion of a protein by the fusion of nucleotide sequences encoding and expressing said protein, to said secretion signal encoding sequences have been provided.

The DNA sequences of the expression system were derived from gene Y isolated from the filamentous fungus P. chrysogenum. Gene Y is highly expressed in P. chrysogenum and Y is efficiently secreted into the culture broth. Expression of a protein of interest is achieved by fusion of the open reading frame encoding a protein of interest to gene Y sequences. Fusions are made by using a variety of molecular genetic techniques which are well known in the art. The structure of the fusion genes can vary significantly depending on the site of fusion of the sequences encoding the protein of interest to gene Y sequences. By analogy to other expression systems it might be necessary to construct different fusion genes and to determine experimentally the optimal fusion construct for expression (M. Ward et al., Biotechnology 8 (1990), 435–440; and patent application WO 90/15860). In a preferred embodiment of the invention the fusion gene encodes the amino acid sequence:

Met-Gln-Ile-Thr-Thr-Val-Ala-Leu-Phe-Leu-Phe-Ala-Ala-Met-Gly-Gly-Val-Ala-Thr-Pro-Ile-Glu-Ser-Val-Ser-Asn-Asp-Leu-Asp-Ala-Arg-Ala-Glu-Ala-Gly-Val-Leu (see SEQ ID NO: 1) (one letter code), or functional parts thereof, as a secretion signal. Fusion constructs are transformed into a filamentous fungus host, preferably P. chrysogenum, most preferably in a non-penicillin producing strain of P. chrysogenum, by methods known in the art. Transformants are selected by using a fungal selection marker such as the S. hindustanus phleomycin resistance gene (Drocourt et al., Nucl. Acids Res. 18 (1990), 4009), the A. nidulans amdS gene (Beri and Turner, Curr. Genet. 11 (1987), 693–641) or the niaD gene (Gouka et al., J. Biotechn. 20 (1991), 189–200) or facA gene (EP-A-91202677.0, to be published) of P. chrysogenum.

Transformants are purified and tested for expression of the protein of interest. Expression of gene Y is subject to glucose repression. Therefore, expression of proteins by using the gene Y expression system is controlled by the amount of glucose in the fermentation medium.

In another aspect of the invention gene Y promoter and terminator sequences are used for regulated, high-level expression of intracellular proteins by omitting the Y secretion signal sequence from the gene fusion. This application can be particularly useful to increase in a controlled manner the concentration of a protein, i.e., penicillin biosynthetic enzymes or proteins which do not occur naturally in P. chrysogenum, such as cephalosporin or cephamycin biosynthetic enzymes. In yet another aspect of the invention gene Y promoter sequences can be very useful as a tool in the isolation and identification of regulatory factors involved in regulation of penicillin biosynthetic genes which are also subject to glucose repression. Common regulatory factors can now be identified and separated from factors involved specifically in regulation of penicillin biosynthetic genes.

Although the gene Y expression system was obtained from P. chrysogenum, it can be used with other filamentous fungus hosts such as Penicillia, Acremonium, Aspergilli, Trichoderma and Mucor with well-known fermentation characteristics. Heterologous expression of promoters, terminators and secretion signals is a common observation in studies on gene expression in filamentous fungi. Alternatively, gene Y homologues can now easily be detected and isolated from other fungal species by using P. chrysogenum gene Y sequence as a probe or by using the Polymerase Chain Reaction (PCR) method and gene Y-derived oligonucleotide probes.

The cloned gene Y of P. chrysogenum can also be used to create mutant Y genes with improved expression and/or secretion characteristics by using molecular genetic techniques well known in the art. It is also recognized that hybrid sequences for expression and secretion of proteins can be obtained by combining i.e. gene Y secretion signal sequences with other promoter or terminator sequences. Gene Y promoter, secretion signal and terminator sequences, or functional parts thereof, can be regarded and applied as individual cassettes in complete expression systems.

Moreover, the invention includes genes with different nucleotide sequences which are homologous to the Y gene of P. chrysogenum or parts thereof. Homology is defined herein as nucleotide sequences which have an identity score of at least 70% in a sequence comparison to gene Y by using the BestFit program of the Wisconsin Sequence Analysis Software Package (version 6.0, release 1989, GCG, University of Wisconsin, USA), using parameter settings gap weight 5.000 and length weight 0.300. Homologous genes may be isolated from natural sources, or may be produced by mutagenesis of gene Y of P. chrysogenum.

In a preferred embodiment proteins are expressed in P. chrysogenum by using homologous gene Y expression signals.

For transformation of Penicillium, constructs are employed including at least one marker for selection of transformed cells and, preferably, for enhancing maintenance of the integrated DNA. Therefore, the vector preferably includes a DNA sequence known to enhance transformation efficiencies. An example of such a DNA sequence is the "ans"-element, isolated from Aspergillus nidulans (cf. Ballance and Turner, Gene 36 (1985) pp. 321–331). The present invention provides a DNA sequence, isolated from the genome of P. chrysogenum, that has been identified as a sequence with an effect similar to the effect of the "ans"

sequence. Since this sequence is native to *P. chrysogenum*, it can be used to increase transformation efficiencies in *P. chrysogenum*. The DNA sequence encompasses the *P. chrysogenum* pyrG gene and can be used either alone, in combination with a PyrG-host in which case said DNA sequence provides both the selection for transformants and the transformation enhancing effect (cf. EP-A-260762), or in combination with another selection marker, e.g. a gene encoding resistance to a biocide, such as phleomycin. In the latter case selection for transformants and the transformation enhancing effect are provided by two separate DNA sequences and the sole function of the pyrG element is to enhance transformation frequencies.

Useful markers for the selection of transformant clones may be homologous or heterologous biosynthetic genes capable of complementing an auxotrophic requirement of the host cell, caused by a defect in a metabolic route to an amino acid, e.g. arginine, a nucleotide precursor, e.g. uracil, and the like.

The structural gene providing the marker for selection may be native to the wild-type Penicillium host or a heterologous structural gene which is functional in the host. For example, structural genes coding for an enzyme in a metabolic pathway may be derived from Penicillium or from other filamentous fungi, e.g., Aspergillus, Neurospora, Podospora, or yeasts, where the structural gene is functional in the Penicillium host and complements the auxotrophy to prototrophy.

The complementing structural gene may be derived from a metabolic pathway, such as the synthesis of purines or pyrimidines (nucleosides) or amino acids. Of particular interest are structural genes encoding enzymes in the pyrimidine pathway, e.g. the gene encoding the enzyme orotidine-5'-phosphate decarboxylase (pyrG or pyr4). Other genes of interest are amino acid biosynthetic genes, e.g. ornithine carbamoyl transferase (araB) and argininosuccinate lyase (arg4). The use of the above-mentioned selection markers is provided in EP-A-260762.

Instead of auxotrophic markers, fermentation markers may be used, such as the capability of using amides as a sole source of carbon or nitrogen, growth on various sugars, e.g. galactose or the like. Furthermore, genes encoding resistance to biocides may be used, such as hygromycin, gentamicin, phleomycin, glyphosate, bialaphos, and the like.

Constructs will be provided comprising the sequence of interest, and may include other functions, such as replication systems in one or more hosts, e.g. cloning hosts and/or the target host for expression of the secondary metabolite; one or more markers for selection in one or more hosts, as indicated above; genes which enhance transformation efficiency; or other specialized function.

The construct may be prepared in conventional ways, by isolating genes of interest from an appropriate host, by synthesizing all or a portion of the genes, or combinations thereof. Similarly, the regulatory signals, the transcriptional and translational initiation and termination regions otainable from gene Y may be isolated from a natural source, be synthesized, or combinations thereof. The various fragments may be subjected to endonuclease digestion (restriction), ligation, sequencing, in vitro mutagenesis, primer repair, or the like. The various manipulations are well known in the literature and will be employed to achieve specific purposes.

The various fragments may be combined, cloned, isolated and sequenced in accordance with conventional ways. After each manipulation, the DNA fragment or combination of fragments may be inserted into the cloning vector, the vector transformed into a cloning host, e.g. *E. coli*, the cloning host grown up, lysed, the plasmid isolated and the fragment analyzed by restriction analysis, sequencing, combinations thereof, or the like.

Various vectors may be employed during the course of development of the construct and transformation of the host cell. These vectors may include cloning vectors, expression vectors, and vectors providing for integration into the host or the use of bare DNA for transformation and integration.

The cloning vector will be characterized, for the most part, by a marker for selection of a host containing the cloning vector and optionally a transformation stimulating sequence, may have one or more polylinkers, or additional sequences for insertion, selection, manipulation, ease of sequencing, excision, or the like.

Expression vectors will usually provide for insertion of a construct which includes the transcriptional and translational initiation region and termination regions; alternatively the construct may lack one or both of the regulatory regions, which will be provided by the expression vector upon insertion of the sequence encoding the protein product.

The DNA encoding a protein of interest may be introduced into a Penicillium host in substantial accordance with the procedure as described in EP-A-260762.

Efficient transformation of Penicillium is provided to produce transformants having one or more structural genes capable of expression, particularly integrated into the host genome (integrants). DNA constructs are prepared which allow selection of transformed host cells. Conditions are employed for transformation which result in a high frequency of transformation, so as to ensure selection and isolation of transformed hosts expressing the structural gene(s) of interest. The resulting transformants provide for stable maintenance and expression of the integrated DNA. It will be appreciated that the transformed host according to the invention can be used as starting strain in strain improvement processes other than DNA mediated transformation, for instance, protoplast fusion, mass mating and mutation. The resulting strains are considered to form part of the invention. The genes of interest to be introduced by transformation may form an integral part of the transformation vector, but it will often be more convenient to offer these genes on a separate vector in the transformation mixture, thus introducing the said genes by cotransformation along with the selective vector, which is a fairly efficient process in filamentous fungi (P. J. Punt et al., Gene 56 (1987) pp. 117–124; K. Wernars et al, Mol. Gen. Genet. 209 (1987) pp. 71–77; L E. Mattern et al., Mol. Gen. Genet. 210 (1987) pp. 460–461).

As a result of the transformation, there will be at least one copy of the gene(s) of interest frequently two or more, usually not exceeding about 100, more usually not exceeding about 10. The number will depend upon whether integration or stable episomal maintenance is employed, the number of copies integrated, whether the subject constructs are subjected to amplification and the like.

The subject invention exemplifies a method to efficiently express proteins in a filamentous host such as *P. chrysogenum*, using regulatory sequences obtainable from gene Y. The invention provides conservative mutations, where the sequence may have as many as 30% different bases, more usually not more than about 10% different bases, or mutations which are non-conservative.

The isolation of the Y gene allows use of the regulatory elements of the Y gene, such as a promoter, an upstream activating sequence (UAS), a terminator and the like, for identification of other specific regulatory sequences by means of standard techniques as gel retardation, crosslinking, DNA footprinting and the like. Isolation of the specific regulatory protein by affinity chromatography will result in the cloning of the gene encoding said protein and subsequent manipulation in a suitable host.

The following examples are offered by way of illustration and not by way of limitation of the *P. chrysogenum* acyltransferase gene.

EXAMPLES

Procedures in this application for gene cloning, gene characterization, gene manipulation and gene handling are well known in the art and adequately described in i.e. Sambrook et al. (Molecular Cloning, a Laboratory Manual, Cold Spring Harbor, USA, 1989).

The mutant strain npe10, obtained from *P. chrysogenum* Wisconsin 54–1255, has been deposited at the Centraal Bureau voor Schimmelcultures, Oosterstraat 1, 3742 SK Baarn, The Netherlands on Mar. 13, 1990, under accession No. CBS 143.90.

EXPERIMENTAL

Example 1

Construction of a Genomic Library of *Penicillium chrysogenum*

A genomic library of *Penicillium chrysogenum* (ATCC 28089) was constructed in substantial accordance with methods known in the art (T. Maniatis et al., (1982), Molecular cloning, A Laboratory Manual, Cold Spring Harbor Laboratory, N.Y.). Chromosomal DNA was extracted from *Penicillium chrysogenum* by forming protoplasts from the mycelium as previously described in EP-A-260762, which disclosure is incorporated herein by reference.

The protoplasts were then lysed by diluting the isotonic (0.7M KCl) suspension with four volumes of TES buffer (0.05M Tris-HCl pH 8.0, 0.1M EDTA, 0.15M NaCl). To the lysate, 1% sodium lauryl sulphate was added and the mixture was incubated at 55° C. for 30 min. After one extraction with phenol and two extractions with chloroform, the DNA was precipitated with ethanol, dried, and dissolved in TE buffer (10 mM Tris, 1 mM EDTA pH 8.0). The DNA solution was then treated with 100 µg/ml RNase at 37° C. for 1 h and subsequently with 200 µg/ml proteinase K at 42° C. for 1 h. The solution was extracted once with phenol and twice with chloroform. An equal volume of isopropanol was layered on top of the aqueous phase and the DNA was collected at the interface by spooling around a glass rod. After drying, the DNA was dissolved in TE buffer. The molecular weight of the DNA preparation thus obtained was about $10^8$. The DNA was partially digested with Sau3A, ligated to dephosphorylated EMBL 3 arms cut with BamHI (Promega Biotec, Madison, Wis., USA), and packaged into bacteriophage lambda capsids using the Packagene System of Promega Biotec. All reactions were carried out in accordance with the manufacturer's recommendations except that the packaging reaction was carried out at 22° C. for 2–3 hours. Libraries were amplified by plating the packaged phages, incubating for 7–8 hours at 37° C. and eluting the phages using 4 ml of SM buffer (0.1M NaCl, 0.01M MgSO₄, 0.05M Tris HCl pH 7.5, 0.01% gelatin) per Petri plate.

Example 2

Isolation of Genes Specifically Expressed During Penicillin Biosynthesis Using a Differential Screening Procedure Genes that are specifically or predominantly expressed during penicillin biosynthesis were identified by probing the genomic library of Example 1 with labelled cDNA probes synthesized on mRNA templates extracted from producing (lactose-grown) and non-producing (glucose-grown) mycelia, and selecting the clones that gave predominantly a positive signal with the former (+) probe.

Messenger RNAs were isolated from cultures grown 3 or 6 days in the production medium (cf. Example 3) (+ preparation) or in the same medium with the lactose replaced by glucose (− preparation). The mycelia were collected by filtration, frozen in liquid nitrogen, homogenized and the mRNA isolated using the guanidinium isothiocyanate method as described by T. Maniatis et al. (vide supra).

cDNAS were synthesized and labelled to a high specific activity with [α-$^{32}$P] dATP against both mRNA populations in a reaction mixture of 30 µl containing

| 12.5 | mM | MgCl$_2$ |
| 50 | mM | Tris-HCl pH 8.3 |
| 100 | mM | KCl |
| 125 | mM | DTT |
| 2 | u/µl | RNasin |
| 500 | µM | dGTP |
| 500 | µM | dCTP |
| 500 | µM | dTTP |
| 25 | µM | dATP |
| 0.2 | µg/ml | BSA |
| 100–200 | µg/ml | poly A$^+$RNa |
| 50–60 | µg/ml | oligo dT$_{12-18}$ |
| 1.2 | u/µl | reverse transcriptase |
| 1.67 | µCi/µl | [α-$^{32}$P] dATP | in which the PolyA+ RNA and oligo-dT were mixed separately, heated to 100° C. for 1 minute, and cooled in ice water prior to adding to the reaction mixture. After 1.5 hours incubation at 42° C., 5 µl of 1 mM dATP was added and the incubation continued for 30 min. Subsequently, the reaction mixture was made 20 mM in EDTA, 40 mM in NaOH (final volume 100 µl) and heated to 65° C. After 1 hour incubation, 5 µl 1M Tris-HCl pH 8.3, 40 µl 0.1N HCl, 7 g calf thymus DNA, 100 µl TES buffer (10 mM Tris, 1 mM EDTA, 1% SDS pH 7.5) and 200 µl 5M ammonium acetate were added and the DNA was precipitated with 800 µl ethanol for 16 hours at −20° C.

The precipitate was collected by centrifugation, washed with 70% ethanol, dried, and dissolved in 32.5 µl of TE buffer (10 mM Tris, 1 mM EDTA pH 8.0). The (+) cDNA preparation was then enriched for sequences specifically expressed during penicillin biosynthesis by two successive rounds (cascades) of hybridization against a (−) mRNA preparation in a reaction mixture of 75 µl containing

| 32.5 µl | (+) cDNA |
| 10 µl | (−) mRNA (1 g/l) |
| 30 µl | 1M NaPO$_4$ pH 6.8 |
| 1.5 µl | 10% SDS |
| 1 µl | 0.5M EDTA |

After incubation for 16 hours at 68° C., 102 µl of water was added (final phosphate concentration 170 mM) and the mixture passed through an hydroxylapatite column equilibrated in 170 mM phosphate at 680° C. Under these conditions, double stranded nucleic acids bind to the column whereas single stranded nucleic acids are eluted. The eluate was collected, dialyzed against TE buffer for 1.5 hours, and ethanol-precipitated after addition of 4 g carrier (calf thymus) DNA. This procedure was repeated and the final unbound cDNA was directly used as a probe to screen a genomic library of the Penicillium strain as follows:

A sample of the amplified library of Example 1 was plated onto 5 Petri plates so as to contain approximately 1500 plaques per plate. The plaques were transferred in duplicate to Gene Screen Plus filters (New England Nuclear) according to the manufacturer's recommendations. One set of filters was probed with the labelled, enriched (+)cDNA preparation; the duplicate set was probed with the labelled (−)cDNA as a control. Positive plaques were purified and subjected to a second screening. In this way, 96 plaques were selected that gave a positive signal predominantly with the (+)cDNA probe.

DNAs of recombinant phages that had given a strong or moderate signal in the initial screening were labelled with $^{32}p$ and used as probes to screen Northern blots of Penicillium RNAs isolated from producing and non-producing mycelia, in order to establish the levels of expression under both conditions. In this way the recombinant clones were divided into three groups:

Class 1 contains genes highly expressed during penicillin biosynthesis and is exemplified by clones G2 and B21
B9, L5 and G5
L12
K9

Class 2 moderately expressed, exemplified by

C12
P3 and K11
B13
B20

Class 3 weakly expressed, exemplified by

| | |
|---|---|
| * G3 | |
| * G1 | * K16 |
| * L10 | * B23 |

Clones G2 and B21 gave a positive hybridization signal when probed with an isopenicillin N synthetase-specific probe (S. M. Samson et al., vide supra). Surprisingly, the same clones appeared also to hybridize to an acyltransferase-specific probe (see Example 5).

Example 3

Purification of Acyltransferase

A *Penicillium chrysogenum* strain (ATCC 28089) was inoculated (at $2\times10^6$ conidia/ml) in a complex seed medium containing: corn steep liquor (20 g/l); distiller solubles (20 g/l); sucrose (20 g/l); CaCO$_3$ (5 g/l) (pH before sterilization 5.7). After 36 hours incubation at 25° C., 250 rpm, the resulting culture was used to inoculate twenty volumes of complex production media containing: Corn steep solids (35 g/l); lactose (25 g/l); potassium phenylacetate (2.5 g/l); MgSO$_4$.7H$_2$O (3 g/l); KH$_2$PO$_4$ (7 g/l); corn oil (2.5 g/l); CaCO$_3$ (10 g/l). After incubation for another 48 hours, the mycelium were collected by filtration and the filter cake washed four times with cold 0.15M NaCl.

200 grams (wet weight) of mycelium were suspended in 700 ml of 0.05M Tris-HCl buffer (pH 8) containing 5 mM dithiothreitol (hereinafter referred to as TD buffer) and disrupted in a Braun desintegrator (Braun, Melsungen, F.R.G.) using Ballotini glass beads (Sigma type V, diameter 450–500 μm) for periods of 30 s at intervals of 15 s with refrigeration in an ethanol/dry ice bath. The extract was then centrifuged for 30 min. at 20,000×g. This and all following steps were carried out at 4°–5° C. To 640 ml of the extract, 27 ml of a 10% (w/v) protamine sulphate solution in 0.05M Tris-HCl pH 8 was slowly added. After stirring for 45 minutes, the nucleic acid precipitate was removed by centrifugation at 20,000×g and the supernatant fractionated by precipitation with ammonium sulfate while maintaining the pH of the solution at 8.0 during the ammonium sulfate additions. The fraction precipitating between 40% and 55% saturation was dissolved in TD buffer containing 1M ammonium sulfate and applied to a phenyl-sepharose CL-4B column (1.8×16 cm) equilibrated with the same buffer. The column was washed with TD buffer at a flow of 5 ml/min until no more unbound proteins were released. The acyltransferase then was eluted from the column with 40% ethylene glycol in 0.05M Tris-HCl pH 8.0.

The eluted fractions were assayed for acyltransferase activity by incubating at 25° C. in a reaction mixture containing 0.2 mM phenylacetyl-coenzyme A, 0.2 mM 6-aminope-nicillanic acid, 5 mM dithiothreitol, 0.1M Tris-HCl pH 8.0 and enzyme extract in a final volume of 200 μl. After 10 minutes the reaction was stopped by adding 200 μl methanol. The samples were centrifuged at 5000×g and the penicillin G was assayed in the supernatant by conventional microbiological or chromatographic methods.

The active fractions from the phenyl-sepharose column were pooled and applied to a DEAE-Sephacel column (1.5×20 cm) equilibrated with TD buffer and the acyltransferase activity was eluted with a linear (0–0.25M) gradient of NaCl in TD buffer at a flow rate of 0.25 ml/min. The pooled active fractions were precipitated with 70% ammonium sulfate and the pellet dissolved in 3 ml of TD buffer and applied to a Sephadex G-75 (coarse) column (2.6×70 cm) equilibrated with TD buffer. The acyltransferase was eluted using TD buffer at a flow of 9 ml/h and collected in the late part of the eluted fractions as a symmetrical peak of protein corresponding to acyltransferase activity. The final purification was 258-fold.

Example 4

Determination of the Amino-Terminal Amino Acid Sequence of Acytransferase and Design of the Corresponding Oligonucleotide Probe Mixtures The enzyme preparation, obtained as described in Example 3 was run on an SDS-PAGE gel (U. K. Laemmli, Nature, 227 (1970) pp. 680 ff) (13% acrylamide, 50 mA). A 29 kD-band (about 10 g of protein) was cut out of the SDS-gel and the protein was electrophoretically transferred onto a PCGM-2 membrane (polybrene impregnated glassfiber, Janssen, Beerse, Belgium), using a Multiphor II Nova blot unit (LXB; 0.8 mA/cm2; 90 min; electrode buffer 5 mM sodium borate pH 8.0). After blotting, the PCGM-membrane was washed four times with 25 mM NaCl, 10 mM sodium borate, pH 8.0 and air dried. The PCGM-adsorbed protein band thus obtained was analyzed for N-terminal amino acid sequence, using a gasphase sequenator (Applied Biosystems model 470 a). The following sequence (SEQ ID NO: 20) was determined:

thr-thr-ala-tyr-cys-gln-leu-pro-asn-gly-ala-leu-gln-gly-gln-asn-trp-asp

According to the underlined part of this amino acid sequence, the following sets of oligodeoxyribonucleotides were synthesized (SEQ ID NO: 21):

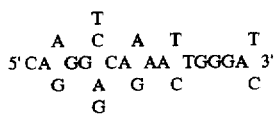

The amino-terminal amino acid sequence of a 10 kD band sometimes present in the preparation was also determined, but not used for the construction of an oligodeoxyribonucleotide probe. The sequence (SEQ ID NO: 22) obtained is:

Met-Leu-His-Ile-Leu-X-Gln-Gly-Thr-Pro-Phe-Glu-Ile-Gly-Tyr-Glu-His-Gly-Ser-Ala-Ala-Lys-Ala-Val-Ile-Ala.

Example 5

Identification of the Acyltransferase Gene

The DNA of a number of the lambda clones of Example 2 was digested with restriction endonuclease SalI, the fragments separated on a 0.7% agarose gel, transferred to Genescreen Plus and hybridized to the [$^{32}$P]-end labelled oligonucleotide mixtures of Example 4. The clones giving a positive signal were mapped by restriction analysis using standard methods. The oligo-deoxy-ribo-nucleotide mixture hybridized specifically to the EcoRI/HindIII subfragment indicated on the map. This and the adjacent fragments were recloned in pTZ 18/19 (United States Biochemical Corporation) and subjected to nucleotide sequence analysis.

The amino-terminal amino acid sequence of a 10 kD band also present in the preparation was determined and found to correspond to a DNA sequence upstream of the 29 kD sequence. Therefore, AT is probably synthesized as a 40 kD protein. This notion is confirmed by the length of the AT messenger, which was demonstrated to be 1500 bases (similar to the isopenicillin N synthetase mRNA which encodes a 38 kD protein), thus allowing for 3' and 5' untranslated regions of 100 bases.

The amino acid sequences of the 29 kD (which has been extended to (SEQ ID NO: 23)

Thr-Thr-Ala-Tyr-Cys-Gln-Leu-Pro-Asp-Gly-Ala-Leu-Gln-Gly-Gln-Asn-Trp-Asp-Phe-Phe-Ser-Ala-Thr-Lys-Gln-Ala)

and 10 kD proteins revealed the presence of two introns. A third intron is postulated on the basis of the gross amino acid composition of the 10 kD protein (97 residues) and on the consensus sequence for its boundaries (D. J. Ballance, Yeast (1986) 2:229–336). The presence of this third intron was confirmed by primer extension and Northern blot hybridization using oligonucleotide probes from coding and non-coding regions.

Example 6

Construction of pPS47

The phosphoglycerate kinase (pgk) gene was isolated from a Penicillium genomic library by standard methods (Maniatis; Example 1), using the corresponding yeast gene (Hitzeman et al., vide supra) as a hybridization probe. The pgk promoter region is located directly upstream of the pgk coding region. The P. chrysogenum pgk promoter was cloned into pTZ18R as a 1.5 kb HindIII fragment and a clone having the desired orientation was selected.

Subsequently, the phleomycin resistance gene was cloned into the BamHI site of the polylinker of this clone as a 1.0 kb BamHI plus BglII fragment, isolated from pUT702 (Cayla, Toulouse Cedex, France). The pgk promoter was fused in-frame to the phleomycin resistance gene, by looping out the sequence to be deleted using an oligonucleotide with the sequence (SEQ ID NO:24)

5'-GGA ACG GCA CTG GTC AAC TTG GCC ATG GTG GGT AGT TAA TGG TAT G-3'

Moreover, this oligonucleotide introduces an NcoI site at the position of the ATG (underlined).

Example 7

Construction of a Transformation Vector with a High Transformation Efficiency rDPS 54)

In order to obtain a transformation frequency of P. chrysogenum that is sufficiently high to allow introduction of genes by transformation or cotransformation with the aim of complementing or amplifying non-selectable genes involved in β-lactam biosynthesis, it is desirable to include in the transformation vector a transformation enhancing sequence (cf. ans in Aspergillus, (Ballance and Turner, Gene (1985) 36:321–331). Surprisingly, a transformation-stimulating sequence which is functional in P. chrysogenum is present on a 2.4 kb EcoRI DNA fragment containing the P. chrysogenum pyrG gene. This DNA fragment forms part of a 4 kb Sau3A partial fragment, cloned in the BamHI site of plasmid pUC13 (Messing, in Meth. Enzymol. (Acad. Press, 1983) 101:20 ff.). This plasmid is referred to as pUC13::pyrG hereinafter (see EP-A-260762).

The 2.4 kb EcoRI fragment was included in a plasmid (pPS47) containing the phleomycin-resistance gene of Streptoalloteichus hindustanus under the control of the promoter of the phosphoglycerate kinase (pgk) gene from P. chrysogenum. The resulting construct is pPS54.

The stimulatory effect of the pyrG fragment on the frequency of transformation is shown in Table 1 below:

TABLE 1

| Plasmid | transformants/μg DNA |
|---|---|
| pPS 47 (phleo$^R$) | 37 |
| pPS 54 (phleo$^R$, pyrG) | 186 |

Example 8

Biological and Biochemical Verification of the Identity of the AT Clones

The identity of the AT clones was biologically verified by complementation of an acyltransferase-negative mutant of P. chrysogenum Wis 54–1255, npe8. 2×10$^7$ protoplasts of an uracil-requiring derivative of strain Wis 54–1255 npe8, Wis 54–1255 npe8 pyrG (CBS 512.88), were cotransformed with a mixture of 5 μg of the selective plasmid pUC 13::pyrG and 15 μg of lambda B21 DNA as described in EP-A-260762. Several hundreds of transformants were obtained. The conidia of these transformants were collected and plated onto the complex production medium of Example 1 at a density of 1–10 colonies per petri dish. After 3 days incubation at 25° C., the plates were overlayered with a spore suspension of a penicillinsensitive Bacillus subtilis indicator strain and incubated overnight at 30° C. to determine the size of the inhibition zones in the bacterial lawn.

Most (75%) of the transformants showed very small haloes, similar in size to the penicillin non-producing recipient stain npe8 pyrG. The remaining 25% showed large inhibition zones comparable to those of the wild-type strain, Wis54–1255. It was concluded that the former class had received only the selective plasmid pUC13::pyrG, whereas the latter had received both pUC13::pyrG and lambda B21, which restores penicillin productivity.

For several transformant clones from both groups, the level of AT-activity in cell-free extracts was determined as follows: mycelia were collected after two days growth as described in Example 3, washed, frozen in liquid nitrogen and pulverized. For each assay, 2.5 grams of ground mycelium were suspended in 50 mM potassium phosphate buffer (pH 8.0) containing 5 mM dithiothreitol and 5 nM EDTA (final volume 12.5 ml) and stirred for 25 minutes. The cell-free extract was obtained by centrifugation of the suspension (5 minutes at 1000×g).

AT-activity was assayed by incubating 2 ml of cell-free extract with 0.1 ml dithiothreitol (10 mg/ml), 0.2 ml 6-aminopenicillanic acid (10 mg/ml) and 0.2 ml phenylacetylcoenzyme A solution (20 mg/ml) at 25° C. After 15 or 30 minutes, the reaction was stopped by adding an equal volume of methanol and the sample centrifuged (20 minutes at 5000×g). The supernatant was then assayed for production of penicillin G by chromatographic (HPLC) methods known in the art. The results of a typical experiment are shown in Table 2 below. These data show that in transformed strains (3 and 4) the level of AT activity is increased 2–3 fold over that of the wild-type (5), consistent with the increased gene dosage.

The IPNS plus AT cluster was subcloned into pPS54, yielding pGJ01 A and B. A 5 kb SalI fragment was made blunt by the action of T4 DNA polymerase and ligated into the unique HindIII site of pPS54, after treatment of this vector with T4 DNA polymerase.

TABLE 3

| Strain | Relative production of penicillin |
|---|---|
| Wis 54-1255 | 100 |
| Wis 54-1255::pRH05 | 122 |

The increased gene dosage of gene Y in the transformant, as compared to the untransformed host, was confirmed by Southern blot analysis. As shown by the results, the increased gene dosage of gene Y, a cryptic gene, isolated by the method of the invention, results in a substantial increase in penicillin production.

The transcript size for gene Y has been determined by Northern blot hybridization: the transcript is about 1.0 kb long.

Example 10

Gene Y

The isolation of gene Y, by using a differential screening method has been described in detail in EP-A-354624. Gene Y was initially isolated on recombinant lambda phages B9, L5 and G5 (EP-A-354624) containing genomic DNA of *P. chrysogenum* and mapped to a 4 kilobase (kb) SphI restriction fragment. The gene Y containing SphI restriction fragment of lambda G5 was subcloned into vector pTZ18Rtm (Pharmacia, Sweden), in two orientations. The resulting plasmids have been named pRH01 and pRH02, respectively.

Plasmid pRH01 is shown schematically in FIG. 1. Plasmids pRH01 and pRH02 have been used to generate a more detailed restriction map of the 4 kb *P. chrysogenum* derived DNA (FIG. 1) and to locate gene Y by hybridization analysis

TABLE 2

| STRAIN | TRANSFORMED WITH | HALO: | UNITS* PEN-G FORMED PER MG PROTEIN, | | NUMBER OF AT COPIES AS ESTIMATED BY SOUTHERN HYBRIDIZATION |
|---|---|---|---|---|---|
| | | | AFTER 15 minutes | AFTER 30 minutes | |
| 1) Wisp 54-1255 npe 8 pyrG | pUC 13::pyrG | − | passes test | 0.9 | 1** |
| 2) idem | puC 13::pyrG plus lambda | − | 1.7 | 1.1 | 1** |
| 3) idem | idem | + | 11.9 | 9.5 | >1 |
| 4) idem | idem | + | 10.8 | 7.0 | >1 |
| 5) Wisp 54-1255 not transformed | | + | 4.5 | 2.7 | 1 |

*relative AT activity in extract
**inactive by mutation

Example 9

Increased Penicillin Production in a Host Strain Transformed with the Cryptic Gene Y To show the effect of the genes identified herein as involved in penicillin production, the gene dosage of one of these genes was increased in a Penicillium host strain. To this end the gene "Y", contained in lambda clones B9, L5 and G5, was subcloned as a 3.0 kb BamHI plus SphI fragment into pPS47. The resulting construct, pRH05 was transformed to *P. chrysogenum* Wis 54–1255 (ATCC 28089) and phleomycin resistant clones were isolated. Several clones were tested for penicillin production in shake flasks.

The results obtained for one transformant isolated are shown in Table 3 below.

more precisely to a 1.2 kb SacI-HindIII restriction fragment near the centre of the 4 kb SphI fragment. Single stranded cDNA prepared as described in EP-A-354624 for differential screening was used as a probe. The direction of transcription of gene Y was also determined by hybridization analysis from SacI (5') to HindIII (3') restriction sites by using the same probe and single-stranded DNA derived from plasmids pRH01 and pRH02. Plasmids pRH01 and pRH02 were used to determine the nucleotide sequence of a 1.5 kb region encompassing the SacI-HindIII restriction fragment (SEQ ID NO: 1).

The sequence analysis was performed according to procedures well known in the art (Sanger et al., Proc. Nat. Acad. Sci. USA 74 (1977) 5463–5467).

Example 11

Gene Y cDNA

Gene Y cDNA has been obtained by using a PCR strategy. PCR technology and other procedures for cDNA cloning, characterization, handling and manipulation are well known and adequately described in Sambrook et al. (supra) and Innis et al. (PCR Protocols, a Guide to Methods and Applications, Academic Press, 1990)

Total RNA was isolated from a penicillin producing culture of P. chrysogenum by using RNAzol™ (Cinna/Biotecx Lab. Int. Inc., Texas, USA), following the instructions of the manufacturers.

tion with ethanol. After centrifugation the pellet was resolved in 10 μl of H20 giving an mRNA/cDNA hybrid concentration of approximately 0.5 mg/ml.

Oligonucleotides were chemically synthesized on a DNA synthesizer (Applied Biosystems, Calif., USA). The sequence of the oligonucleotides, shown in Table 4, is derived from the genomic sequence of gene Y, listed in SEQ ID NO: 1.

TABLE 4

Nucleotide sequence of oligonucleotides used for cDNA synthesis and nucleotide sequence analysis Oligo

AB2277 (SEQ ID NO: 5) 5'-CCC GGG ACT AGT ATG CAA ATC ACC ACA GTT GCC-3'

AB2278 (SEQ ID NO: 6) 5'-CCC GGG ACT AGT ATG ACC CTC AAT TCC ATA TAG-3'

AB2280 (SEQ ID NO: 7) 5'-CCC GGG GGA TCC TCA CAG GGC ATC TCG CAT ATC-3'

AB2308 (SEQ ID NO: 8) 5'-CCC GGG ACT AGT GCC AGT CAC CGT GTC AAG CGT-3'

AB2309 (SEQ ID NO: 9) 5'-CCC GGG ACT ACT CCA CCC GTA AGA ATA TAC CAG-3'

AB2312 (SEQ ID NO: 10) 5'-CCC GGG ACT ACT TTG GAC CTG AGC ATT GTA TGT-3'

AB2313 (SEQ ID NO: 11) 5'-CCC GGG GGA TCC GAT GGG AGT GAT ACT ATA TGG-3'

AB 2314 (SEQ ID NO: 12) 5'-CCC GGG ACT AGT ATA TCC CAT ACC TTA AGT ACT-3'

AB2315 (SEQ ID NO: 13) 5'-CCC GGG GGA TCC AGT ACT TAA GGT ATG GGA TAT-3'

AB2316 (SEQ ID NO: 14) 5'-CCC GGG GGA TCC TAT TTA CAT TCG TTC TTA GAT-3'

AB2317 (SEQ ID NO: 15) 5'-CCC GGG GGA TCC GTT CTT TGT GGG TGT AGG GTA-3'

AB2319 (SEQ ID NO: 16) 5'-CCC GGG GGA TCC ACG ATC AAA AGA TGC TGG ATA-3'

AB2425 (SEQ ID NO: 17) 5'-CCC GGG ACT AGT TAT AGT ATC ACT CCC ATC ACA-3'

AB2426 (SEQ ID NO: 18) 5'-GGG CTT GAG ATG ATG ATC-3'

Reverse-primer (SEQ ID NO: 19)
5'-AAC AGC TAT GAC CAT-3'

PolyA+ RNA was isolated from total RNA by oligo-dT cellulose chromatography using an mRNA purification kit (Pharmacia, Sweden). Approximately 60 μg of polyA+ RNA was isolated from approximately 200 μg of total RNA and dissolved into 200 μl of RNase free H20.

Synthesis of mRNA/cDNA hybrids was done by using Reverse Transcriptase and by using oligo-dT as a primer. A typical reaction contained: 17 μl of polyA+ mRNA, 1.9 μl of RNAsin (40 U/μl, Promega, USA), 10 μl of 5× RT buffer (250 mM Tris.HCl, pH 8.3, 15 mM MgC12, 375 mM KCl), 10 μl of 50 mM DTT (dithiothreitol), 5 μl of 8 mM dNTP-mix (dATP, dCTP, dTTP, dGTP at a concentration of 8 mM each), 5 μl of BSA (bovine serum albumin (1 mg/ml, Sigma, USA)), and 2.5 μl of Moloney Reverse Transcriptase (200 U/μl, BRL, FRG).

The reaction mixture was incubated at 37° C. for 60 minutes with an extra aliquot of 1 μl of Reverse Transcriptase added after 30 minutes of incubation. The reaction was stopped by adding 50 μl of H20, 10 μl of 0.2 M EDTA and 110 μl of chloroform to the reaction mixture. Nucleic acids were purified by chloroform extraction and precipita- Oligonucleotides contained usually 21 nucleotides complementary to gene Y and a flanking sequence of 12 nucleotides containing SpeI and SmaI or BamHI and SmaI restriction enzyme recognition sites, respectively. Oligonucleotides were dissolved in 10 mM Tris.HCl, pH 8.0, 1 mM EDTA. Optimal concentrations for PCR were determined by electrophoresis on 4% Nu Sieve-GTG (FMC, USA) agarose gels in 1× TBE buffer (45 mM Tris.borate, 1 mM EDTA, pH 8.0; Sambrook, supra) and by PCR experiments.

PCR was used to isolate gene Y cDNA. A typical PCR reaction contained (50 μl volume): 5 μl of 10× R buffer (500 mM KCl, 100 mM Tris.HCl, pH 8.3, 20 mM MgC12, 0.1% (w/v) gelatin, 8 μl of a dNTP mixture (1.25 mM each of dATP, dCTP, dGTP and dTTP), optionally, 5 μl of DNA-dilution buffer (10 mM Tris.HCl, pH 8.0, 1 mM EDTA, 10 mM NaCl), approximately 0.05–0.1 μg of mRNA/cDNA hybrid, approximately 0.5 μg of oligonucleotide (each), and H20 to make the final volume 50 μl.

PCR was performed by using 1.3 units of Taq DNA Polymerase and a PCR apparatus (DNA thermal cycler, Perkin Elmer Cetus, USA). Approximately 20–25 cycles were performed, depending on the length of the fragment (per cycle: 2 minutes 94C; 2 minutes 55-C; 3 minutes 72 C, depending on the length of the fragment). In the last cycle the denaturation step was omitted. PCR products were analyzed by electrophoresis on 1.4% Nu Sieve agarose gels in 1× TBE buffer. PCR products were purified by extraction with chloroform, precipitation with ethanol and by using a RDP Mini column (Bio-Rad, Calif., USA). PCR products were finally dissolved in H2O, digested with restriction enzymes SpeI and HI, and ligated into SpeI, µHI digested pBluescript II KST™ vector (Stratagene, Calif., USA) following standard cloning procedures. E. coli strains HB101 (Boyer et al., J. Mol. Biol. 41 (1969), 459–465; and Sambrook et al., supra) or WK6 (Zell and Fritz, EMBO J. 6 (1987, 1809–1815) were used for transformation and plasmid propagation. The nucleotide sequence of cloned PCR fragments was determined by using double-stranded plasmid DNA or by isolating plasmid derived single-stranded DNA by superinfection of transformants with helper phage M13K07 (Vieira, J., Meth. Enzymol. 153 (1987), 3–11) and by application of several oligonucleotides, both pBluescript derived and gene Y derived, following procedures well known in the art (Sanger, supra).

The nucleotide sequence of gene Y cDNA, compiled from sequences of several different, overlapping PCR fragments is shown in SEQ ID NO: 3. The amino acid sequence deduced from the cDNA sequence is shown in SEQ ID NO: 1.

Example 12

Functional Structure of Gene Y

The functional structure of gene Y is summarized in SEQ ID NO: 1.

Nucleotides 1 to 1514 indicate the genomic sequence of gene Y. Nucleotides 553 to 628 and 719 to 786 indicate the position of two introns which disrupt the open reading frame (ORF). Two in-frame ATG start codons are found at positions 427–430 and 466–469, respectively, an UAG stop codon is found at position 847–849, which confines, the ORF to nucleotides 427 to 849 or nucleotides 466 to 849, depending on the ATG codon used. The ORF identified encodes a small, cysteine-rich protein of 55 amino acids with an calculated molecular weight (MW) of 10013 D.

The N-terminal amino acid has a high content of hydrophobic amino acids typical for leader sequences involved in secretion. Nucleotides 1 up to 426 define (part of) the region required for initiation of transcription (promoter) and 5'-end processing of Y mRNA (non-translated leader), and is referred to as transcription initiation regulating sequence. Within this sequence typical promoter elements have been recognized: a CAATbox at nucleotides 225–228 and a TATA box at nucleotides 312–315 followed by a pyrimidine-rich sequence.

The region required for termination of transcription and 3'-end processing of Y mRNA is confined to nucleotides 850 up to 1514, and is referred to as transcription termination regulating sequence.

Example 13

Expression of Y

P. chrysogenum strains were cultured on a standard complex medium (Revilla et al., J. of Bacteriol. 168 (1986), 947–952; and Revilla et al., J. Antibiot. 37 (1984), 781–789), containing either glucose or lactose as defined carbon source. After a period of 2–5 days total RNA was isolated from the mycelium as described in Example 2.

Samples, containing approximately 20 µg of total RNA were denatured by using glyoxal and DMSO (Sambrook, supra) and subjected to electrophoresis on 1.0% agarose gels in 10 mM phosphate buffer pH 7.0.

Following electrophoresis, RNA was blotted onto nylon membranes (GeneScreen+, New England Nuclear, USA) according to the instructions of the manufacturer. Northern blots were then probed with a mixture of two probes, both labelled by using a random priming labelling kit (Boehringer) and [$^{32}$P] dATP (3000 Cu/mmol, Amersham, UK). Probe 1, the 4 kb SphI restriction fragment of plasmid pHRO1 (Example 1), was used to detect Y mRNA. Probe 2, the 1.2 kb HindII restriction fragment of plasmid pGJ02 (Veenstra et al., J. Biotechnol. 19 (1990), 81–90), was used to detect PENDE mRNA. The latter probe generates by crosshybridization a signal with 5S rRNA as well (Veenstra et al., In: 50 Years of Penicillin Application, Symposium in Honour of Sir Edward P. Abraham, Sep. 8, 1990, Berlin, FRG) which is used as a control for the amount of RNA loaded. Standard, stringent, conditions for hybridization and washing of the membranes have been maintained (Sambrook, 1989, supra).

Figure 2A:
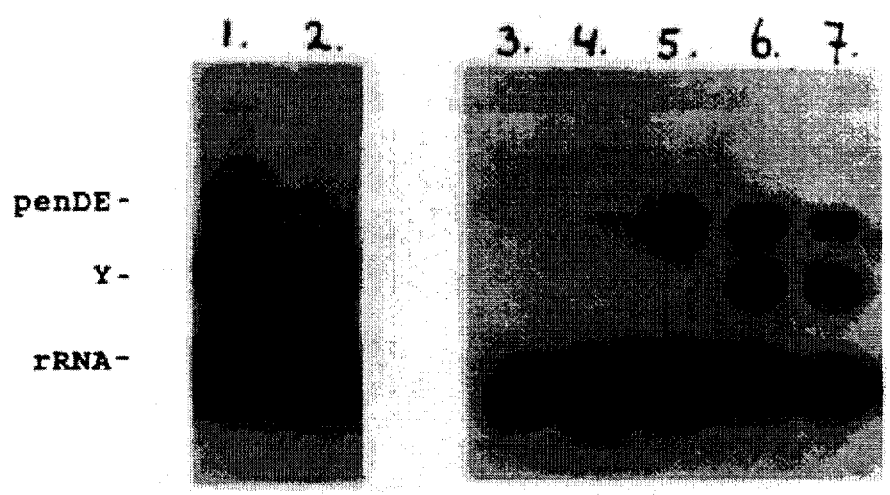
FIG. 2A shows a Northern blot analysis of gene Y expression; lane 1: *P. chrysogenum* Wisconsin 54–1255/lactose; lane 2: *P. chrysogenum* npelO/lactose; lanes 3–7: *P. chrysogenum* Wisconsin 54–1255 on saturating (lanes 3–4) and limiting (lanes 5–7) amounts of glucose.

Typical results, are shown in FIG. 2A which demonstrates the high level of Y mRNA compared to PENDE mRNA. Expression of gene Y is repressed by the presence of excess glucose and derepressed and/or induced by the absence of excess glucose. Furthermore, efficient and regulated expression of gene Y is also observed in strain npelO, a non-penicillin derivative of P. chrysogenum Wisconsin 54–1255 lacking the PcbAB-pcbc-PENDE gene cluster (EP-A-448180).

Figure 2B:
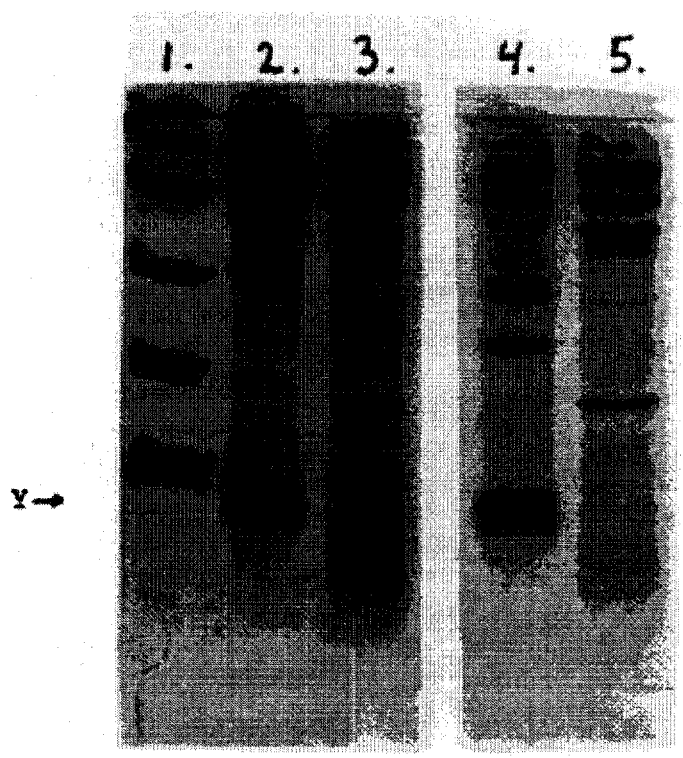
FIG. 2B shows a SDS-PAAGE analysis of broth proteins; lane 1: molecular weight markers (LNW markers 94.000/67.000/43.000/30.000/20.100/14.400, Pharmacia, Sweden); lanes 2–3: *P. chrysogenum* Wisconsin 54–1255 broth from glucose (lane 3) and lactose (lane 2) cultures; lanes 4–5: *P. chrysogenum* npelO broth from glucose (lane 5) and lactose (lane 4) cultures.

The expression of gene Y was also investigated at the protein level by analysis of proteins present in the broth of P. chrysogenum cultures. Broth samples were filtrated and concentrated by precipitation with methanol. The protein composition of the filtrate was analyzed on denaturing 17.5–20% PAAGE (acrylamide:bisacrylamide 39:1 w/w) 0.1% SDS slab gels, run in Tris.glycine-SDS buffer (25 mM Tris, 192 mM glycine, 0.1% SDS, pH 8.5) according to Laemlli (Nature 227 (1970), 680–685). Following electrophoresis proteins were stained in situ with Coomassie Brilliant Blue R250 and photographed. A typical result is shown in FIG. 2B. It is clear from FIG. 2B that a protein of the expected size of approximately 8 kD is highly expressed under conditions of Y mRNA expression. In addition to the strains shown in FIG. 2B, P. chrysogenum strains containing multiple copies of gene Y, obtained by transformation of gene Y, showed an increased level of 8 kD protein in culture filtrates.

Example 14

Identification of Y

The identification of the 8 kD protein in culture filtrates of P. chrysogenum as the Y gene product was achieved by partial N-terminal amino acid sequence analysis. P. chrysogenum strain Wisconsin 54–1255 was grown as described in Example 4 under Y expressing conditions (lactose as defined carbon source). Culture broth was collected, filtrated, concentrated and proteins were separated on denaturing SDS-PAAGE gels as described in Example 4. Following electrophoresis proteins were blotted onto a PVDF membrane (polyvinylidene difluoride, 0.45 µm pore size, Millipore, Mass., USA) using a semi-dry blotting system (Nova blot, LKB, Sweden). After blotting proteins were visualized by staining with Coomassie Brilliant Blue R250. Membrane sections containing the 8 kD protein were collected and used for Nterminal sequence analysis by the Edman degradation procedure using an automatic analyzer (Applied Biosystems, USA). The amino acid sequence determined is shown in SEQ ID NO: 4. The sequence analysis proves the identity of the 8 kD protein as the Y gene product. Amino acids 1 to 21 of the mature secreted Y correspond to amino acids 38–58 of the ORF starting at the first ATG codon (see Example 3 and SEQ ID NO: 1). The leader sequence for processing and secretion of Y is hereby confined to the sequence of amino acids -37-1 listed in SEQ ID NO: 1.

Example 15

Phytase Expression in *Penicillium chrysogenum* by Using Gene Y Expression Signals A *P. chrysogenum* phytase expression cassette is constructed by fusion of sequences of the phytase gene of Aspergillus ficuum encoding the mature form of phytase (EP-A-420358) to expression signals of gene Y, i.e. the promoter, secretion signal and terminator sequences of gene Y. The fusion is made by application of the PCR method (Innis, supra) and results in the replacement of nucleotides 538 to 846 in SEQ ID NO: 1 with nucleotides 382 to 1715 of the phytase gene sequence published in FIG. 6 of EP-A-420358. Plasmids pRH01' (FIG. 1) and pAF2-2S (EP-A-420358) are used in PCR experiments. The resulting plasmid pPYPH01 contains the Y-phytase gene fusion as well as the *S. hindustanus* phleomycin resistance gene under control of the promoter of the phosphoglycerate kinase (PGK) gene of *P. chrysogenum* pPYPH01 is introduced into *P. chrysogenum* by transformation according to procedures well known in the art (Veenstra et al., supra). Transformants are selected for resistance to phleomycin, purified and then analyzed for expression of phytase by methods described in detail in EP-A-420358.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. An isolated DNA comprising a nucleotide sequence obtainable from gene Y which regulates transcription initiation of a DNA sequence of interest operably joined to said nucleotide sequence.

2. The isolated DNA according to claim 1, wherein said nucleotide sequence comprises nucleotide 1 up to nucleotide 426 of SEQ ID NO: 1.

3. An isolated DNA comprising a nucleotide sequence obtainable from gene Y which regulates transcription termination of a DNA sequence of interest operably joined to said nucleotide sequence.

4. The isolated DNA according to claim 3, wherein said nucleotide sequence comprises nucleotide 850 up to nucleotide 1514 of SEQ ID NO: 1.

5. An isolated DNA comprising a nucleotide sequence obtainable from gene Y which encodes a secretion signal sequence.

6. The isolated DNA according to claim 5, wherein said nucleotide sequence comprises nucleotide 427 up to nucleotide 537 of SEQ ID NO: 1.

7. A DNA construct comprising a first nucleotide sequence obtainable from gene Y which regulates transcription initiation, a second nucleotide sequence obtainable from gene Y which regulates transcription termination, and a DNA sequence of interest operably fused to said first and second nucleotide sequences wherein at least one of said first and second nucleotide sequences and said DNA sequence of interest does not occur naturally with one or more of the remaining sequences.

8. The DNA construct according to claim 7, wherein said DNA construct further comprises a third nucleotide sequence obtainable from gene Y and encoding a secretion signal sequence operably joined between said first nucleotide sequence and said DNA sequence of interest.

9. A method for obtaining expression and secretion of a protein encoded by a DNA sequence of interest, said method comprising:

growing a host containing a DNA construct according to claim 8, under conditions whereby said protein is expressed and secreted.

10. A method for obtaining expression of a DNA sequence of interest, said method comprising:

growing a host containing a DNA construct according to claim 7, under conditions whereby said DNA sequence of interest is expressed.

11. The method according to claim 10 or 9, wherein said host is a filamentous fungus host.

12. The method according to claim 11, wherein said filamentous fungus host is *Penicillium chrysogenum*.

13. An isolated DNA comprising:

a nucleotide sequence which encodes an amino acid sequence which functions as a secretion signal sequence, wherein said amino acid sequence comprises Met-Gln-Ile-Thr-Thr-Val-Ala-Leu-Phe-Leu-Phe-Ala-Ala-Met-Gly-Gly-Val-Ala-Thr-Pro-Ile-Glu-Ser-Val-Ser-Asn-Asp-Leu-Asp-Ala-Arg-Ala-Glu-Ala-Gly-Val-Leu-- (a.a.s -37 to -1 of SEQ ID NO:2).

14. A DNA construct comprising:

a first nucleotide sequence obtainable from gene Y which regulates transcription initiation, a second nucleotide sequence which regulates transcription termination and a DNA sequence of interest operably joined to said first and second nucleotide sequences, wherein at least one of said first and second nucleotide sequences and said DNA sequence of interest does not occur naturally with one or more of the remaining sequences.

15. The DNA construct according to claim 14, wherein said DNA construct further comprises a third nucleotide sequence obtainable from gene Y and encoding a secretion signal sequence operably joined between said first nucleotide sequence and said DNA sequence of interest.

16. A method of obtaining expression of a DNA sequence of interest, said method comprising:

growing a host containing a DNA construct according to claim 14, under conditions whereby said DNA sequence of interest is expressed.

17. A method for obtaining expression and secretion of a protein encoded by a DNA sequence of interest, said method comprising:

growing a host containing a DNA construct according to claim 15 under conditions whereby said protein is expressed and secreted.

* * * * *